US006576894B1

(12) United States Patent
Doong

(10) Patent No.: US 6,576,894 B1
(45) Date of Patent: Jun. 10, 2003

(54) STRUCTURE FOR FIB BASED MICROANALYSIS AND METHOD FOR MANUFACTURING IT

(75) Inventor: Yih-Yuh Doong, Kaohsiung (TW)

(73) Assignee: Taiwan Semiconductor Manufacturing Company, Hsin-Chu (TW)

( * ) Notice: Subject to any disclaimer, the term of this patent is extended or adjusted under 35 U.S.C. 154(b) by 213 days.

(21) Appl. No.: 09/888,469

(22) Filed: Jun. 25, 2001

(51) Int. Cl.[7] .......................... H01J 49/00; G01N 23/00
(52) U.S. Cl. ........................ 250/282; 250/307
(58) Field of Search ................. 250/282, 305, 250/306, 307, 311, 492.1, 492.21, 492.23, 492.3; 216/33, 36, 39

(56) References Cited

U.S. PATENT DOCUMENTS

| | | | |
|---|---|---|---|
| 5,270,552 A | * 12/1993 | Ohnishi et al. | 250/307 |
| 5,369,274 A | * 11/1994 | Brunger | 250/306 |
| 5,440,123 A | * 8/1995 | Ikeda | 250/307 |
| 5,977,543 A | * 11/1999 | Ihn et al. | 250/311 |
| 6,015,976 A | * 1/2000 | Hatakeyama et al. | 250/492.23 |
| 6,042,736 A | * 3/2000 | Chung | 216/33 |

* cited by examiner

Primary Examiner—Hai Pham
(74) Attorney, Agent, or Firm—George O. Saile; Stephen B. Ackerman

(57) ABSTRACT

Microanalysis of small areas on insulating substrates can be a problem because of charge and thermal buildup. One solution has been to coat the underside of the area with a layer of thermally and electrically conductive material. This becomes very difficult to do when there is no clear access to the surface in question. The present invention solves this problem by forming two cavities, on opposite sides of the area that is to be microanalyzed, that extend downwards into the substrate at an angle to its surface so that they intersect directly below the microanalysis area. The result is a cavity that is bridged by a beam having a triangular cross-section. Part of said beam is then selectively removed, resulting in a cantilever that extends out over the cavity with the microanalysis area located near its free end. Coating of the cantilever's underside is achieved by using a focused ion beam to first deposit the layer in question on the two lower sloping surfaces of the cavity. Then, as a result of sputtering by the ion beam itself, some of this material is ejected and redeposits on the underside of the beam.

20 Claims, 3 Drawing Sheets

STRUCTURE FOR FIB BASED MICROANALYSIS AND METHOD FOR MANUFACTURING IT

FIELD OF THE INVENTION

The invention relates to the general field of microanalysis based on focused ion beams, with particular reference to samples that are insulators.

BACKGROUND OF THE INVENTION

Charging effects and thermal damage are typical problems in most samples examined by charged particle microscopy, when the current level is in the nanoampere or microampere range. These current levels severely degrade the image resolution and several methods have been developed to solve the problem. These include:

a. Coating a thin film of high conductivity/thermal conductive material on the specimen surface
b. Operation at low beam energy,
c. Incorporating a second beam of ion (for scanning electron microscope or SEM) or electrons (for focused ion beam or FIB) to discharge the specimens (charge compensation or charge neutralization). The ion or electron beam is called a flood gun. Particularly for the glass specimens such as TFTs (Thin Film Transistor) on glass, ultraviolet light is used to discharge the accumulated charge.

Coating techniques are the most popular of the above methods for charged-particle microscopy. Among the different coating techniques we may mention:

1. Surfaces coating: vacuum evaporation and sputter coating technique which are standard procedure in most electron microscopy and analytical laboratories.
2. Metal impregnation from fixative solutions of Os(osmium) and Mn(manganese), with or without the use of organic metal ligands or mordants such as thiocarbohydrazide, galloglucose, paraphenylenediamine, by exposing specimens to OS40 vapor or by bulk staining the specimens after fixation with metallic salts.
3. Spraying or impregnating with organic anti-static agents derived from polyamines, e.g. Duron, Denki, or sodium alk-benzene sulfonate, soaking in conducting colloids of noble metals or graphite or covering the sample with a thin (1–20 nm) polymer film such as Formvar or styrene vinylpryidine.

These operations are not suitable for samples which cannot be coated at the surface that is being examined, such as insulators, or samples for AES (Auger electron microscopy), SIMS (Secondary Ion Mass Spectrometry), and EDX (energy-dispersed spectroscopy of X-rays).

An earlier invention by the present inventor disclosed how the problem of charge and heat buildup on insulating specimens could be mitigated. In U.S. Pat. No. 5,474,803, Doong showed a method in which a rectangular cavity was formed directly underneath the sample area. The cavity wall closest to the sample was then coated with a conductive material so that electric charge and heat could leak to it for dissipation. Coating of this surface with the required material required that the substrate be accurately cut very close to the sample area to allow formation of and access to the cavity. Additionally, for two different sample areas that were close together, one would have to be sacrificed during the process of preparing the other.

A routine search of the prior art was performed and the following references of interest were also found:

In U.S. Pat. No. 5,977,543, Ihn et al. show a sample preparation method for charged particle microscopy. In U.S. Pat. No. 5,369,274 Brunger, and in U.S. Pat. No. 5,440,123 Ikeda, both show microscope methods, specifically substrate preparation.

SUMMARY OF THE INVENTION

It has been an object of the present invention to provide a structure that is suitable for the performance of microanalysis over a small area.

Another object of the invention has been that structure allow the microanalysis of insulating areas without the buildup of excess heat or electric charge.

A further object has been that structure make it possible to successively remove thin slices of the area under microanalysis.

A still further object has been to provide a process for the manufacture of said structure.

Still another object has been that said process enable the underside of a portion of the structure to coated with a layer of material even though there is another surface in close proximity to it.

These objects have been achieved by forming two cavities, on opposite sides of the area that is to be microanalyzed, that extend downwards into the substrate at an angle to its surface so that they intersect directly below the microanalysis area. The result is a cavity that is bridged by a beam having a triangular cross-section. Part of said beam is then selectively removed, resulting in a cantilever that extends out over the cavity with the microanalysis area located near its free end. A key feature is that the underside of the beam is coated with a layer of thermally and electrically conductive material. This is achieved by using a focused ion beam to first deposit the layer in question on the two lower sloping surfaces of the cavity. Then, as a result of sputtering by the ion beam itself, some of this material is ejected and redeposits on the underside of the beam.

DESCRIPTION OF THE PREFERRED EMBODIMENTS

Figure 1:
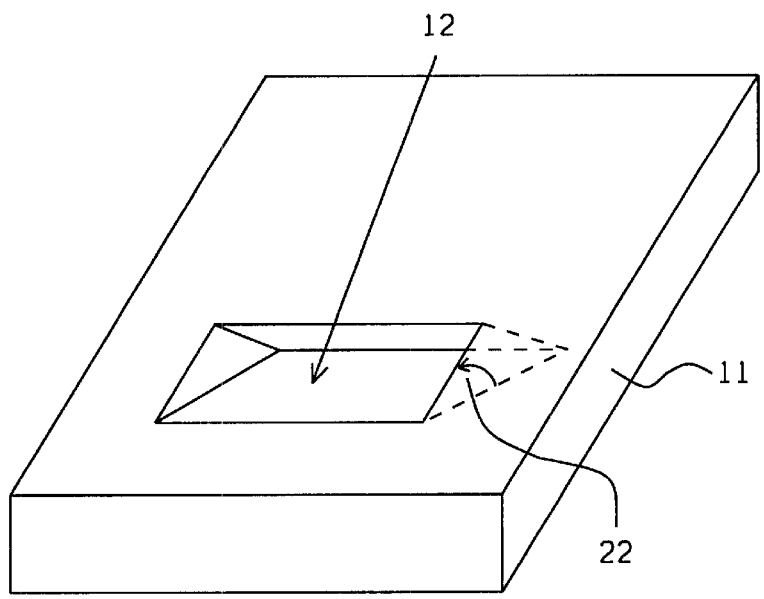
FIG. 1 shows the starting point of the process.

We will describe the present invention in terms of the process for its manufacture. This will also serve to describe the structure of the present invention. Referring now to FIG. 1, the invention begins with the provision of substrate 11 which could be of conductive or insulating material and which will generally be a portion of a larger substrate that includes an area that is to be microanalyzed.

Figure 2:
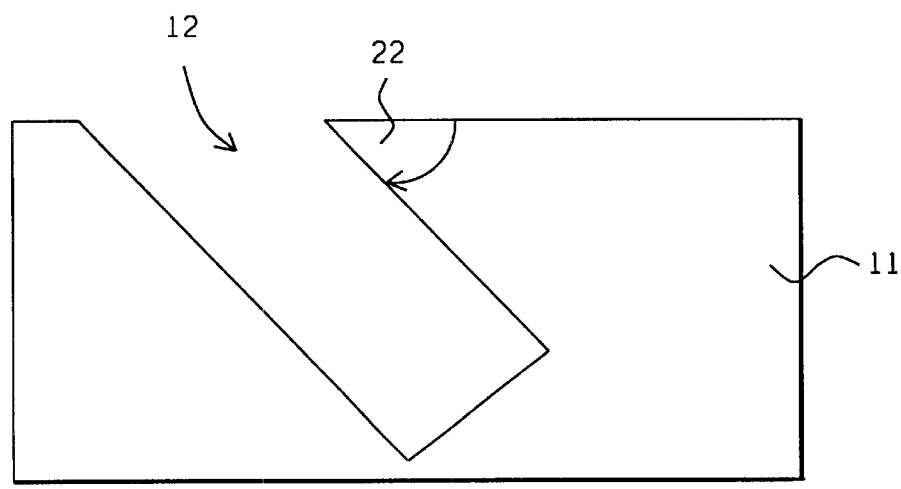
FIG. 2 is a cross-sectional view of a cavity formed within a substrate at an angle to the surface.

Cavity 12 is then formed using ion beam milling or a similar technique. This cavity has a rectangular cross-section and extends downwards into the substrate from the upper surface of substrate 11 at angle θ (22) relative to the surface. Typically, angle θ is between about 15 and 45 degrees. FIG. 2 is a cross-sectional view of the isometric projection shown in FIG. 1.

Figure 3:
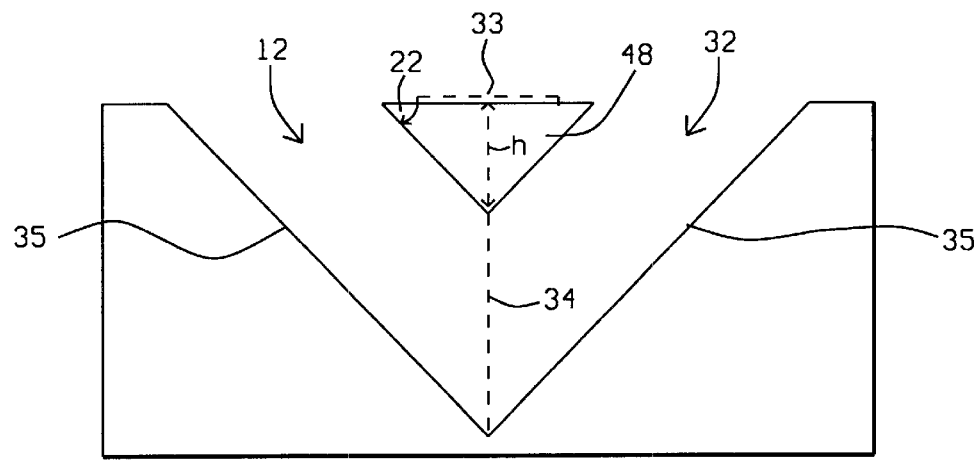
FIG. 3 shows the effect of forming a second cavity that intersects the first one beneath the surface.
Figure 5:
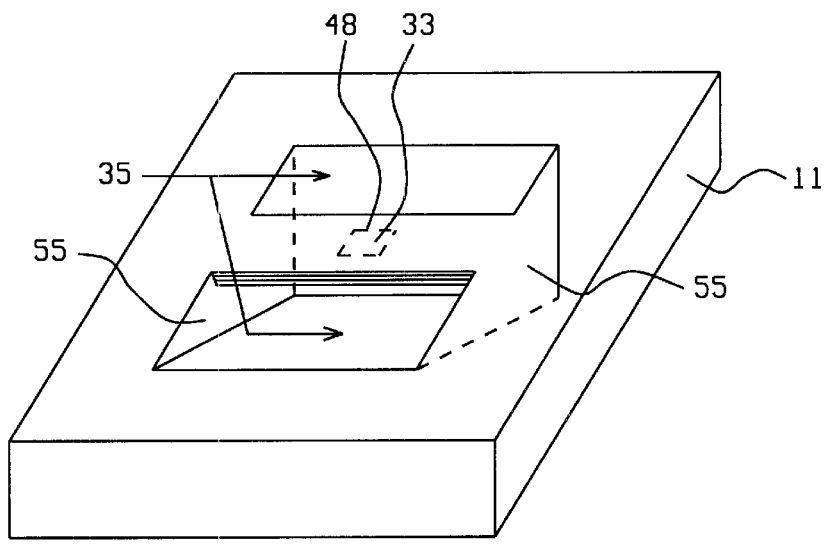
FIG. 5 is an isometric view of the structure of FIG. 4.

Then, as shown in FIG. 3, second cavity 32 is formed in the same manner as was cavity 12 but sloping in from the opposite side with care being taken to ensure that area 33 that is to be microanalyzed is located mid-way between the inner edges of the two cavities; that is, directly over line 34 which marks the line of intersection of the two cavities. The degree of precision that is attainable using the ion beam milling is such that the area that is to be microanalyzed can have an area that is at least h×cot θ microns wide (where h is the height of triangular bridge 48 as seen in FIG. 3). Once cavities 12 and 32 intersect, a larger cavity having sloping sidewalls 35 gets formed. This larger cavity can be seen by looking ahead to FIG. 5 which is an isometric projection. At this stage of the process it has two vertical opposing triangular sidewalls 55, separated by a distance that ranges from less than a micron to several microns, depending on the resolution of the FIB. These are connected by the sloping sidewalls 35. Also connecting the triangular sidewalls 55 is bridge 48 which also has a triangular cross-section and a top surface that is coplanar with that of the substrate 11.

Figure 4:
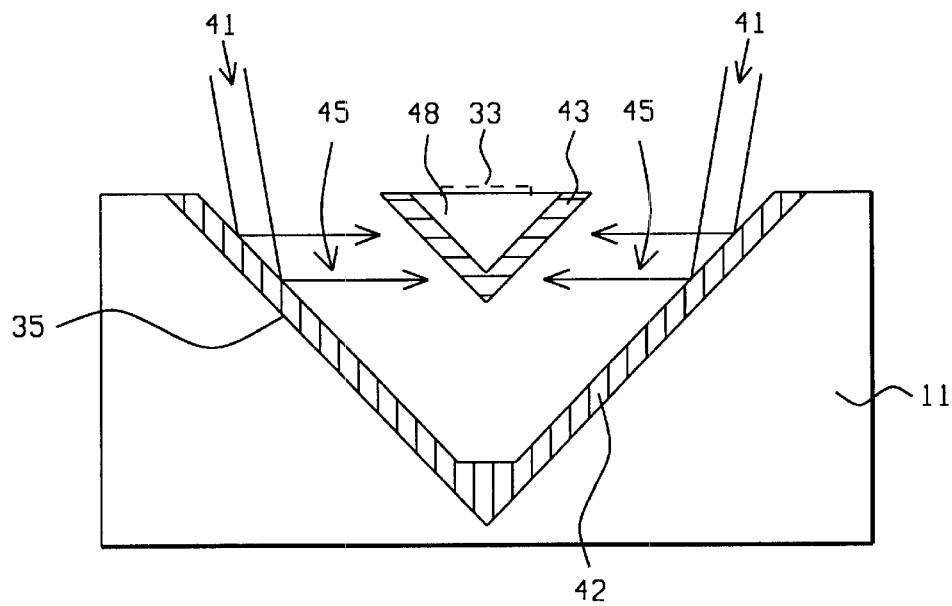
FIG. 4 shows how both upper and lower surfaces of the cavity seen in FIG. 3 can be coated with a suitable layer.

Now follows a key feature of the invention, as illustrated in FIG. 4. Focused ion beam 41 is used to deposit layer 42 of electrically and thermally conductive material onto the sloping sidewalls 35. Any of the following materials would be suitable for layer 42: tungsten, platinum, carbon, gold, and copper which, at the completion of deposition, has a thickness between about 100 Angstroms and 1 micron. The focused ion beam has a mean particle energy between about 100 eV and 30 keV volts and a mean current density between about 10 pA and 1 $\mu$A. Since an ion beam is being used, some of the material that deposits onto sidewalls 35 gets ejected through sputtering by the same beam 41. This is shown schematically as beam 45 of ejected material which gets re-deposited on the underside of bridge 48 to form layer 43. At the conclusion of the process, layer 43 has a thickness between about 100 and 5,000 Angstroms. The initial beam current is low (10 pA to 500 nA) to deposit some material. It is then changed to a higher current density (100 nA to 1 $\mu$A) to sputter material onto layer 43.

Figure 6:
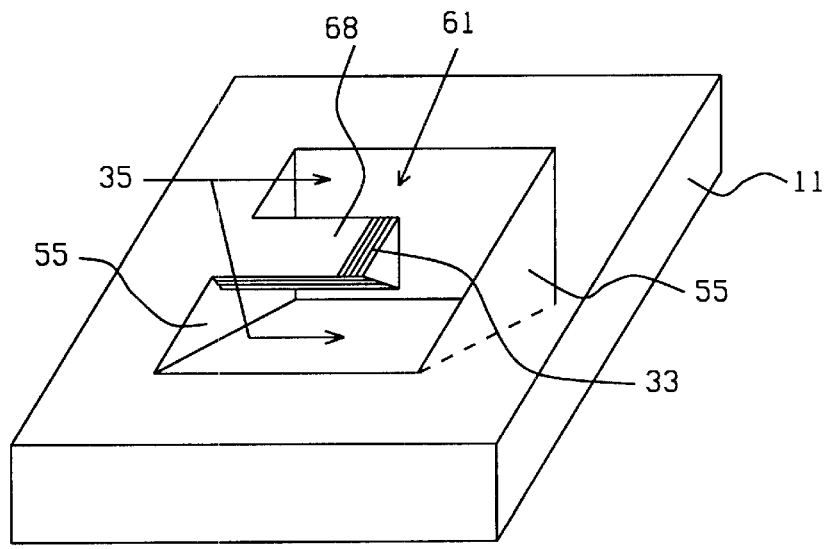
FIG. 6 is the final structure at the end of the formation process.

The next step in the process is illustrated in FIG. 6. Once bridge 48 has been formed, a portion of it on one side is selectively removed by FIB selective etching or selective ion sputtering, resulting in the formation of cantilever beam 68. Beam 68 is attached to one of the vertical side-walls 55 and extends outwards therefrom in a direction that is parallel to intersection line 34 (see FIG. 3). The cutting of 48 to form 68 is such that the area to be microanalyzed, 33, ends up being located near the cantilever's free end.

The structure is now ready for the performance of microanalysis in area 33. Among the types of microanalysis that may be performed are included Auger electron microscopy, Secondary Ion Mass Spectrometry, and energy-dispersed spectroscopy of X-rays. An important advantage of the use of this type of structure for microanalysis is that it allows for the successive removal of vertical slices from the cantilever's free end schematically shown as slices 61 in FIG. 6.

While the invention has been particularly shown and described with reference to the preferred embodiments thereof, it will be understood by those skilled in the art that various changes in form and details may be made without departing from the spirit and scope of the invention.

What is claimed is:

1. A process for preparing an area for microanalysis, comprising:

providing a substrate having an upper surface that includes said area that is to be microanalyzed;

forming a first cavity, having a rectangular cross-section, that extends downwards into the substrate from the upper surface at an angle thereto;

forming a second cavity, having a rectangular cross-section, that extends downwards into the substrate from the upper surface at said angle, whereby said cavities intersect and terminate along a line that is directly beneath said area to be microanalyzed, with said area being approximately located above the center of said line, thereby forming a third cavity, that has first and second opposing triangle-shaped vertical side-walls connected by sloping rectangular side-walls, said vertical side-walls being connected by a bridge of substrate material having a triangular cross-section and an underside;

using a focused ion beam, coating said sloping side-walls with a layer of an electrically and thermally conductive material while simultaneously coating said bridge underside with material sputtered out of the layer by said focused ion beam;

selectively removing a portion of the bridge, between the area to be microanalyzed and the first vertical side-wall, thereby forming a cantilever that is attached to the second vertical side-wall, the area to be microanalyzed being located near the cantilever's free end; and then performing the microanalysis.

2. The process described in claim 1 wherein the first and second cavities are formed by means of ion beam milling.

3. The process described in claim 1 wherein the step of performing the microanalysis further comprises implementing a process selected from the group consisting of Auger electron microscopy, Secondary Ion Mass Spectrometry, and energy-dispersed spectroscopy of X-rays.

4. The process described in claim 1 wherein said focused ion beam has a mean particle energy between about 100 eV and 30 keV.

5. The process described in claim 1 wherein said focused ion beam has a mean current density between about 10 pA and 1 $\mu$A.

6. The process described in claim 1 wherein the layer is selected from the group consisting of tungsten, platinum, carbon, gold, and copper.

7. The process described in claim 1 wherein the layer on said sloping side-walls is deposited to a thickness between about 100 and 10,000 Angstroms.

8. The process described in claim 1 wherein the layer on said bridge underside is deposited to a thickness between about 100 and 5,000 Angstroms.

9. The process described in claim 1 wherein the angle between the substrate and the first and second cavities is between about 15 and 45 degrees.

10. The process described in claim 1 further comprising, as part of said microanalysis step, successively removing vertical slices from the cantilever's free end.

11. A structure for supporting an area that is to be microanalyzed, comprising:

a substrate having an upper surface;

a cavity that extends downwards from said upper surface;

said cavity having opposing triangle-shaped vertical side-walls, of height h, connected by rectangular side-walls that slope at an angle relative to said upper surface;

said sloping side-walls intersecting along a line having a mid-point;

over, and parallel to, said line, a cantilever beam, having an underside, that extends away from one of said vertical side-walls to a beam end that is above said mid-point;

said beam having an upper surface that is coplanar with the upper surface of the substrate;

on the sloping sidewalls, a first layer of an electrically and thermally conductive material;

on said beam underside, a second layer of an electrically and thermally conductive material; and said area that is to be microanalyzed being located on the beam's upper surface near the beam end.

12. The structure described in claim 11 wherein the cantilever beam has a length that is between less than 1 micron and several microns, depending on sample size.

13. The structure described in claim 11 wherein microanalytical processes that may be performed using the structure are selected from the group consisting of Auger electron microscopy, Secondary Ion Mass Spectrometry, and energy-dispersed spectroscopy of X-rays.

14. The structure described in claim 11 wherein said electrically and thermally conductive layers are selected from the group consisting of tungsten, platinum, carbon, gold, and copper.

15. The structure described in claim 11 wherein the layer on said sloping side-walls has a thickness between about 100 and 10,000 Angstroms.

16. The structure described in claim 11 wherein the layer on said beam underside has a thickness between about 100 and 5,000 Angstroms.

17. The structure described in claim 11 wherein the angle between the substrate upper surface and said sloping side-walls is between about 15 and 45 degrees.

18. The structure described in claim 11 wherein the area that is to be microanalyzed has an area that is greater than said h value times the cotangent of said angle.

19. The structure described in claim 11 wherein said vertical sidewalls are separated by a distance that is between about less than 1 micron and several microns.

20. The structure described in claim 11 wherein the cantilever beam has a triangular cross-section.

* * * * *